United States Patent [19]
Kunze

[11] Patent Number: 5,575,992
[45] Date of Patent: Nov. 19, 1996

[54] EXTENDED RELEASE HOT AND COLD GEL FRAGRANCE CARTRIDGES AND METHOD OF MAKING THE SAME

[75] Inventor: Walter A. Kunze, Southington, Conn.

[73] Assignee: Waterbury Companies, Incorporated, Waterbury, Conn.

[21] Appl. No.: 489,806

[22] Filed: Jun. 13, 1995

Related U.S. Application Data

[62] Division of Ser. No. 207,935, Mar. 8, 1994, abandoned.

[51] Int. Cl.[6] .................................. A61L 9/04; A61L 9/12
[52] U.S. Cl. ........................ 424/76.4; 424/76.3; 422/5; 239/34; 239/60; 512/4; 252/315.1
[58] Field of Search ............................. 424/76.3, 76.4; 422/5; 239/34, 60; 512/4; 252/315.1

[56] References Cited

U.S. PATENT DOCUMENTS

| | | | |
|---|---|---|---|
| 3,990,848 | 11/1976 | Corris | 239/57 |
| 4,157,787 | 6/1979 | Schwartz | 239/60 |
| 4,271,092 | 6/1981 | Sullivan et al. | 261/30 |
| 4,356,969 | 11/1982 | Obermayer et al. | 239/60 |
| 4,387,849 | 6/1983 | Van Loveren et al. | 239/60 |
| 4,624,366 | 11/1986 | Marder et al. | 239/60 |
| 4,743,406 | 5/1988 | Steiner et al. | 261/30 |
| 4,809,912 | 3/1989 | Santini | 239/60 |
| 4,830,791 | 5/1989 | Muderlak et al. | 261/26 |
| 4,840,770 | 6/1989 | Walz et al. | 422/49 |
| 4,865,816 | 9/1989 | Walz et al. | 422/123 |
| 5,060,858 | 10/1991 | Santini | 239/60 |
| 5,230,867 | 7/1993 | Kunze et al. | 422/123 |
| 5,324,490 | 6/1994 | Vlahakis et al. | 422/305 |

Primary Examiner—Amy Hulina
Attorney, Agent, or Firm—St. Onge Steward Johnston & Reens

[57] ABSTRACT

A fragrance dispensing cartridge is disclosed housing either a hot- or cold-type fragrance containing gel. Each gel is housed in a cartridge having an opening, wherein the opening is covered with an air permeable membrane. The membrane is positioned above the gel and permits the fragrant agent to communicate with an environment external to the cartridge housing opening. The composition of the gels and the density and permeability of the membrane can be varied to provide the desired release rate.

6 Claims, 1 Drawing Sheet

EXTENDED RELEASE HOT AND COLD GEL FRAGRANCE CARTRIDGES AND METHOD OF MAKING THE SAME

This application is a divisional of an application having Ser. No. 08/207,935, filed on Mar. 8, 1994, now abandoned entitled "Extended Release Hot and Cold Gel Fragrance Cartridges and Method of Making the Same".

DESCRIPTION

1. Technical Field

The present invention relates to fragrance cartridges for dispensing a vaporizable substance, such as a fragrant oil, wherein the substance is released into the atmosphere to, for instance, overcome undesirable odors typically associated with public restrooms and the like.

2. Background of the Invention

It is known to provide air freshening devices which include a solid or liquid aromatic agent, disposed in a housing so that a surface of the agent is exposed. The fragrance is dispersed passively by the movement of air in the space around the exposed surface of the agent. Alternatively, the housing may be equipped with a fan or other means for generating air movement to accelerate dispersal of the agent. After the agent is exhausted, the device is generally discarded.

Such devices, however, have several disadvantages. For example, the agent can be messy, especially in its liquid form. Considerable caution must thus be exercised to avoid spilling the liquid, especially when opening the device and inserting a refill of the housing. Furthermore, the aromatic agent in these dispensers evaporates quickly, so that large containers and hence cumbersome housings are required if the aromatic agent supply is to last for a longer period of time, such as at least 28 days. Current commercially available liquid aromatic agent dispensers last considerably less time—about fourteen days or less.

One means for avoiding the premature dissipation of an aromatic agent is the provision of a fragrance cartridge, which employs a pad treated with an odoriferous agent. The cartridge generally has a trough-like housing having an open top in which the pad is disposed. The top of the housing is sealed with a permeable material that permits controlled dispersal of the fragrance.

Such cartridge-type air fresheners have several advantages over their more cumbersome counterparts described above in that they are more convenient and less prone to spillage, etc. One cartridge-type device is disclosed in U.S. Pat. No. 5,230,867 to Kunze. This cartridge-type device includes a cartridge containing a polyester pad sealed in the cartridge by a polyester, air permeable membrane. This cartridge device is desirable because it is relatively small, allowing the use of a smaller dispenser, and still has a fragrance release rate of about 28 to 30 days or longer. It has a drawback, however, in that the pad and the cartridge can be expensive and, hence, less commercially appealing. Furthermore, although the use of a treated pad reduces the risk of spillage or leaks, the risk still exists. If such occurs, the pad, in which a liquid aromatic agent is absorbed, can be messy and damaging when the liquid spills in the dispenser, or leaks onto a wall, furniture or the like, or leaks during shipping.

The aforementioned cartridges and other air freshening devices have another drawback in that they are limited in terms of the options available to consumers. For instance, all of the various different combinations of fragrance strength and release rate which may be desired may not be available with a soaked pad cartridge.

What is desired, therefore, is a fragrance dispensing cartridge which uses an economical fragrance containing substance, which is itself relatively small and can be housed in a relatively small dispenser. The desired cartridge includes a fragrance releasing substance which is not prone to spillage, has an effective release rate, and a sufficiently long life. Further, the cartridge can be varied to offer a wide range of options to the consumer, such as a relatively strong odor for a shorter period of time, or a mild odor for a long period of time.

SUMMARY OF THE INVENTION

Accordingly, it is an object of the present invention to provide a fragrance dispensing cartridge which is capable of using an economical fragrance containing substance.

It is another object of the present invention to provide a fragrance dispensing cartridge which is itself relatively small and which can be housed in a relatively small dispenser.

It is still another object of the present invention to provide a fragrance dispensing cartridge which employs a fragrance containing substance which is not prone to spillage.

It is yet another object of the invention to provide a fragrance dispensing cartridge which dispenses a fragrance for a significant period of time, such as about 28–30 days.

It is a further object of the invention to provide a cartridge which can be varied to provide a range of strengths and release rates, such as a relatively strong odor for a short period of time or a relatively mild odor for a long period of time.

It is still a further object of the invention to provide a method of making such a cartridge that includes a fragrance containing substance having a desired odor strength, release rate and cartridge life.

To overcome the deficiencies of the prior art and to achieve the objects and advantages listed above, a fragrance dispensing cartridge is disclosed which includes a cartridge having an opening, a gel containing a fragrant agent housed in the cartridge such that a surface of the gel is exposed through the cartridge opening, and an air permeable membrane covering the cartridge opening for regulating the flow of the fragrant agent from the gel through the membrane to an environment external to the cartridge opening.

In the preferred embodiment of the invention, either a hot-type or a cold-type gel can be housed in the cartridge. The composition of each gel varies depending upon the desired release rate and the permeability of the membrane which covers the cartridge opening. For an effective release rate of about twenty-five to about thirty days, a suitable hot-type gel may comprise at least about fifty percent fragrant agent, at least about fifteen percent gelling agent, at least about three percent encapsulant and, if necessary, a solvent therefor.

Most preferably, the hot-type gel has a release rate of approximately twenty-eight to about thirty days and comprises at least about seventy-two percent fragrance agent, at least about twenty-five percent gelling agent, at least about five percent encapsulant, and if necessary, a solvent therefor.

Any fragrant agent which provides a suitably strong odor for a sufficiently long time will suffice. Advantageously, the agent is an organic oil-based perfume. One suitable oil-based perfume is commercially available as #220-677 Cherry, manufactured by AromaTech of Somerville, N.J. Other suitable perfumes include, but are not limited to, those commercially available as HF-F-91-8432 Cherry, manufactured by Hogan Fragrances of New York, N.Y., and #48-549 Cherry, manufactured by Carrubba, Inc., of Milford, Conn.

The gelling agent is any heat-activated agent which sufficiently solidifies, thickens, hardens or otherwise firms the gel such that it does not seep or otherwise exit through any attached membrane during use or shipping. Typical gelling agents include various commercially available gums and gels. One suitable gelling agent is available as Aromagel made by AromaTech.

The encapsulant employed protects the fragrant agent from degradation by heat or other processing steps. The encapsulant most often forms a "capsule" surrounding the fragrant agent sufficiently to prevent degradation, yet still allows dispersal of the agent through the gel and to the environment. A suitable encapsulant is one in which the fragrant agent becomes suitably coated with or imbedded in a molten film, sheath or foam, such that the encapsulant acts as a semipermeable membrane permitting the release of an enclosed fragrance agent. Suitable encapsulants include gelatin and albumin. Others are polymeric in nature although other materials such as buckminsterfullerenes ("bucky balls") can be employed. Suitable materials are commercially available.

A solvent in which the components of the gel are at least partially solubilized is employed, if necessary. Typical solvents include water and alcohols and mixtures thereof.

Hot-type gels are most often preferred in the present invention, even though the heating adds additional processing step(s). This is because the hot gels, in their finished state, are more solidly gelled than cold-type gels. This reduces the damages of spillage, etc. even further. Contrariwise, cold-type gels often provide higher release rates, and are preferred when high release rates are desired.

The composition of the cold-type gel, to achieve a release rate of about twenty-five to about thirty days, may comprise at least about seventy percent fragrant agent, at least about five percent gelling agent and, if necessary, a solvent therefor. Most preferably, to achieve a release rate of about twenty-eight to about thirty days, the cold-type gel comprises at least about eighty-eight percent fragrant agent, at least about ten percent gelling agent, and, if necessary, a solvent therefore.

As was the case with the hot-type gel, any suitable fragrant agent, which provides a sufficiently strong fragrance for a sufficiently long period of time will suffice. Advantageously, the agent is also an organic oil-based perfume, such as #A1177 Citrus, made by Carrubba Inc. Other suitable fragrant agents include those commercially available as #221-571 Citrus made by Aromatech and #HF-F91-8434 Citrus made by Hogan Fragrances.

The gelling agent can be any agent which sufficiently solidifies, thickens, hardens or otherwise firms the gel composition, with or without the application of heat such that it does not seep or otherwise exit through any attached membrane during use or shipping. A preferred gelling agent includes a carboxymethylcellulose, such as Cab-O-Sil made by Cabot Corp. located in Tuscola, Ill.

Any solvent may be used, if necessary, in which the components of the fragrant agent are at least partially solubilized. Suitable solvents include water and alcohols.

Depending on cost and scent strength, it may be appropriate to mix the perfume in the gel with an odorless extender to prolong the life of the fragrance. A suitable extender for purposes of the present invention, when aromatic organic oil-based perfumes are used are oils, such as Isopar, an odorless mineral oil, manufactured by Exxon Company USA of Houston, Tex.

After the gel is housed in the cartridge, an air permeable membrane is positioned above the gel and covers the housing opening, screening the flow of the fragrant agent. Because the different hot-type gels and the cold-type gels evaporate at different rates, different membranes are combined with each gel to adjust the cartridge life, providing the desired release rate. One suitable membrane for the hot-type gel described above, to achieve an effective release rate of about twenty-five to about thirty days, is a membrane having a density of about 0.3 $oz/yd^2$ to about 0.9 $oz/yd^2$, a permeability of about 800 $CFM/ft^2$ to about 1200 $CFM/ft^2$ and a denier of about 4.0 to about 4.8. Such a membrane is commercially available from Intertech Group, Inc., of Old Hickory, Tenn., and referred to as REEMAY® 2006. A different membrane, such as a different REEMAY® style, can be used with the cold-type gel to achieve the same release rate. The characteristics of the membrane used are "matched" to those of the gel, as would be understood from this disclosure, to provide the release rate of the entire system.

In the preferred embodiment, the average effective cartridge life is about twenty-five to about thirty days. As such, the average release rate of each gel, when used with a suitable membrane, is approximately 0.70 grams per day to about 1.30 grams per day. The composition of the gel employed and physical characteristics of the membrane can be combined to provide this desired release rate.

The composition of each gel can be varied to provide a variety of odor strengths, ranging from a relatively strong odor to a relatively mild odor, as desired. For example, to obtain a stronger odor for a lesser period of time, more fragrant agent can be used. To obtain a milder odor for a longer period of time, more gelling agent can be used. In the alternative, a stronger odor can be provided by a more permeable membrane (with concomitant reduction in cartridge life) or a milder odor with a less permeable membrane (with concomitant increase in cartridge life). Combinations of these factors can be employed to provide a wide range of variation.

A seal, typically made of foil, is secured over the opening of the cartridge housing and above the membrane to prevent the release of the fragrance between the time of manufacture and the time of use. A tab on the seal can facilitate opening of the seal.

BRIEF DESCRIPTION OF THE DRAWINGS

FIG. 2 is a cross sectional view taken along line 2—2 of the cartridge shown in FIG. 1a.

DETAILED DESCRIPTION OF THE DRAWINGS

Figure 1A:
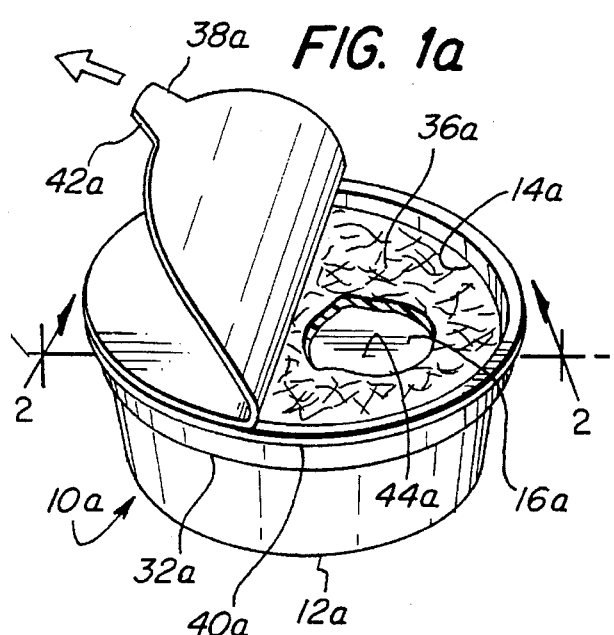
FIG. 1a is a perspective view of a cartridge housing a hot-type gel, constructed in accordance with the present invention, showing a seal partially removed.

Referring to the drawings in detail, a fragrance dispensing cartridge, constructed in accordance with the present invention, is shown and generally designated by the reference numerals 10a, 10b. Cartridge 10a generally comprises housing 12a having opening 14a for housing hot-type gel 16a. See FIG. 1a. Cartridge 10b generally comprises housing 12b having opening 14b for housing cold-type gel 16b. See FIG. 1b.

It should be understood that cartridges 10a, 10b are substantially identical, differing generally in the gel housed in the cartridge. As such, reference may be made only to one cartridge, such as 10a; however, it should be understood that those references are generally equally applicable to the other cartridge, such as 10b.

Figure 3:
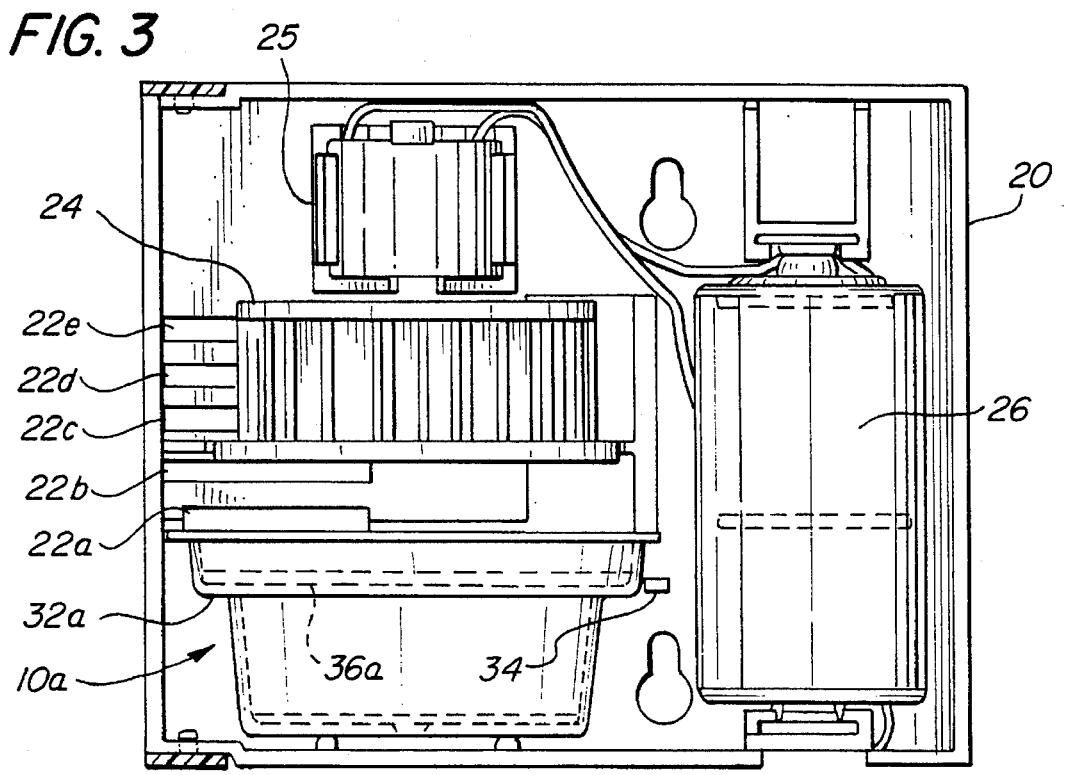
FIG. 3 is a partial cross sectional view of the cartridge shown in FIG. 1a housed in a dispenser.

As shown in FIG. 3, cartridge 10a is generally housed in dispenser 20, which is any suitable dispenser which sufficiently contains cartridge 10a and which sufficiently disperses the aromatic agent in gel 16a (FIG. 1). One suitable dispenser 20 was disclosed by Kunze in a patent application filed on Oct. 15, 1993, entitled "An Apparatus for Inducing Air Flow Past a Cartridge Containing a Vaporizable Substance" and accorded Serial Number 08/138,123, the disclosure of which is hereby incorporated by reference herein.

Dispenser 20 comprises a plurality of inlet and outlet vents, such as 22a, 22b, 22c, 22d, 22e, fan 24 adjacent the vents, and battery 26 for operating motor 25 to operate fan 24. Although any suitable battery will suffice, battery 26 is generally a 1.5 volt DC battery and is designed to operate motor 25 and fan 24 continuously after being operably connected. Cartridge 10a is preferably adjacent to vents 22a, 22b, 22c, 22d, 22e and in relation to fan 24, such that fan 24 pulls air in through at least one inlet vent, such as 22a, 22b, at least partially across cartridge 10a, through housing 20 and radially outward through at least one outlet vent, for example 22d.

Again referencing FIG. 3, shoulder 32a of cartridge 10a acts cooperatively with stake 34, protruding from dispenser 20, and shelves (not shown), to securely position cartridge 10a within dispenser 20. As such, cartridge 10a has relatively little ability to move freely within dispenser 20 even when dispenser 20 is disturbed.

Cartridge 10a contains hot-type gel 16a. See FIGS. 1a, 2, 3. Preferably, hot-type gel 16a comprises at least about fifty percent fragrant agent, at least about fifteen percent gelling agent, at least about three percent encapsulant and, if necessary, a solvent therefor, to achieve a service life of about twenty-five to about thirty days (when used with a suitable membrane as discussed below). Most preferably, hot-type gel 16a comprises about 65%–85% fragrant agent, 20%–30% gelling agent, 2–7% encapsulant and, if necessary, a solvent therefore.

Cold-type gel 16b, housed in cartridge 16b, and shown in FIG. 1b, comprises at least about seventy percent fragrant agent, about at least five percent gelling agent and, if necessary, a solvent therefor, to achieve a service-life of about twenty-five to about thirty days (when used with a suitable membrane, as discussed below). Most preferably, cold-type gel comprises at least about 80–95% fragrant agent, 5–15% gelling agent and a solvent therefor, if necessary.

The composition of gel 16a, 16b is one factor which determines the release rate of the fragrance from the gel. For example, the amount of each ingredient can be varied to provide a different release rate. To obtain a stronger odor for a shorter period of time, more fragrant agent can be used; conversely, less fragrance agent can be used to obtain a milder odor. To obtain a milder odor for a longer period of time, more gelling agent can be used.

Gel 16a, 16b is sealed within housing 12a, 12b by membrane 36a, 36b attached to housing 12a, 12b around shoulder 32a, 32b, respectively. See FIGS. 1a, 1b, 2. Attachment of membrane 36a, 36b to shoulder 32a, 32b can be accomplished in any manner which forms an air tight seal around shoulder 32a, 32b. One method of attachment includes ultrasonic welding. After membrane 36a, 36b is attached to shoulder 32a, 32b, membrane 36a, 36b covers housing opening 14a, 14b but preferably does not contact gel 16a, 16b, respectively.

The properties of membrane 36a, 36b affect the rate of dispersal of the fragrant agent by delimiting the flow of the fragrant agent. If membrane 36a, 36b has a high density and a low permeability, it will retard the dispensing of the fragrance to the atmosphere. If membrane 36a, 36b has a low density and a high permeability, then the fragrance will be released more rapidly.

Any membrane 36a, 36b (FIGS. 1–3) can be used which permits the fragrant agent to communicate with an environment external to the cartridge housing opening 14a, 14b. Preferably, membrane 36a, 36b sufficiently screens the flow of fragrant agent such that the service life of cartridge 10a, 10b is approximately twenty-five to thirty days.

One membrane 36a which achieves about a thirty-day release rate for the hot-type gel 16a is REEMAY® Style 2006, manufactured by Intertech Group, Inc. of Old Hickory, Tenn.

Seal 38a, 38b is secured across opening 14a, 14b, respectively, of housing 12a, 12b and, in particular, is joined to lip 40a, 40b (FIGS. 1a, 1b, 2) for preventing release of the fragrance between the time of manufacture and the time of use. Lip 40a, 40b allows seal 38a, 38b to be bonded thereto in a position away from upper surface 44a, 44b of gel 16a, 16b thereby affording a dry surface for providing a secure, airtight seal.

Seal 38a, 38b can be made of any material which prevents the release of the fragrant agent, but is most preferably made of foil, and is securely bonded to lip 40a, 40b by heat and pressure bonding. Alternatively, ultrasonic welding or an adhesive may be used to make this bond.

Seal 38a, 38b includes tab 42a, 42b (FIGS. 1a, 1b) which can be gripped by a user to remove seal 38a, 38b, respectively to open the cartridge 10a, 10b for dispersal of the fragrance.

Figure 1B:
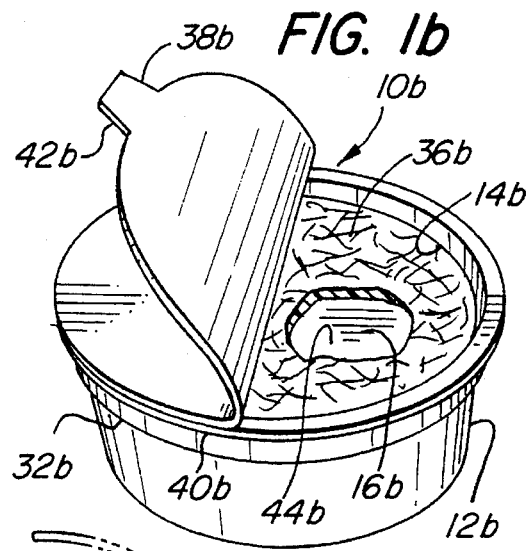
FIG. 1b is a perspective view of a cartridge housing a cold-type gel, in accordance with the present invention, showing a seal partially removed.
Figure 2:
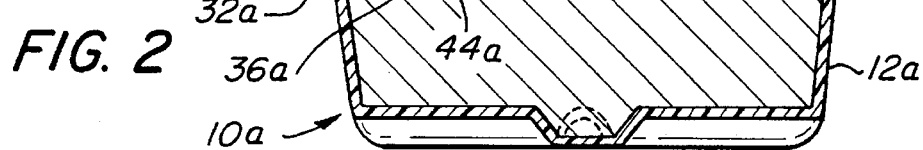

In operation, cartridge, such as 10a, is opened by removing seal 38a by pulling tab 42a in the direction of the arrow, as shown in FIGS. 1a, 2. Cartridge 10a is placed inside dispenser 20, as shown in FIG. 3, and is complimentarily received by shelves (not shown) and stake 34. As such, cartridge 10a is adjacent plurality of inlet and outlet vents 22a, 22b, 22c, 22d, 22e. Fan 24 is activated, causing air to enter through at least one inlet vent, travel at least partially across cartridge 10a through housing 20 and radially outward through at least one outlet vent.

Movement of air across cartridge 10a causes fragrant agent in gel 16a to rise to the upper surface 44a of gel 16a. The rate at which the aromatic agent is drawn to the top surface 44a of gel 16a and released into the environment external to cartridge housing opening 14a depends on the properties of the gel. These properties include, but are not limited to, the type of fragrant agent used and the permeability of the membrane. The average daily release rate for gels 16a, 16b, when used in conjunction with a membrane 36a, 36b is about 0.70–1.3 grams per day.

According to the present invention, the properties of gel 16a, 16b in combination with the properties of membrane 36a, 36b achieve a desired, predetermined rate of fragrance release and cartridge life. Generally, a service life of at least about twenty-five days is easily achieved by the present invention. In fact, in most instances, the service life is about twenty-five to thirty days.

Further, it should be noted that cartridges 10a, 10b provide a plurality of variables which can affect the release rate and, hence, the cartridge life. For example, a gel with a relatively high concentration of gelling agent will have a relatively longer odor-dispensing life than a gel with a lesser concentration of gelling agent (all other things being equal, such as the properties of the membrane 36a, 36b).

Alternatively, the gel composition may remain the same, while the density of membrane 36a, 36b can be varied to provide a cartridge 10a, 10b with a longer or shorter dispensing life, as desired. For example, a membrane with a higher density will retard the flow of the fragrant agent more than a membrane with a lower density. In addition, other membrane properties can be varied. A membrane with a lower permeability will retard the flow of the fragrant agent, while a membrane with a higher permeability will increase the flow of the fragrant agent. Further, the denier can be varied to achieve a desired release rate.

The method of making the fragrance containing hot-type gel 16a generally comprises the following steps. First, at least about fifty percent fragrant agent, at least about fifteen percent gelling agent, at least about three percent encapsulant and, if necessary, a solvent therefor are mixed together. The mixture is then heated to between about 120° F. and about 160° F. until it becomes a liquid blend. Most preferably, the mixture is heated to about 135° F. to about 145° F. Afterwards, the mixture is transferred, or poured, into cartridge housing 12a through opening 14a where it cools and sets. Then, cartridge housing opening 14a is covered with an air permeable membrane 36a. If desired, the cartridge housing opening 14a can be covered with air tight seal 38a, preferably after the liquid blend has been allowed to cool and gel.

The method for making the cold-type fragrance containing gel 16b comprises the steps of mixing together at least about seventy percent fragrant agent, at least about five percent gelling agent and, if necessary, a solvent therefor. Then the mixture is transferred to cartridge housing 12b through opening 14b. Afterwards, opening 14b is covered with air permeable membrane 36b. Seal 38b can then be applied to opening 14b, if desired.

Both hot- and cold-type fragrant gels 16a, 16b become gelled relatively quickly. As such, in this firmed, or hardened, state, gels 16a, 16b do not move to substantial degree within cartridge 10a, 10b. Cartridges 10a, 10b can then be moved, shipped, or otherwise disturbed with a reduced danger of spillage or leaks.

It should be understood by those skilled in the art that obvious modifications can be made without departing from the spirit of the invention. Accordingly, reference should be made primarily to the accompanying claims, rather than the foregoing specification, to determine the scope of the invention.

We claim:

1. A process for making a cartridge containing fragrant gel, comprising the steps of:

mixing together at least about fifty percent fragrant agent, at least about fifteen percent gelling agent, and at least about three percent encapsulant;

heating the mixture to between about 120° F. and to about 160° F. until the mixture becomes a liquid blend;

transferring the liquid blend to a cartridge housing through an opening in the cartridge housing; and covering the cartridge housing opening with an air permeable membrane.

2. The process of claim 1, further comprising the step of adding a solvent to the fragrant agent, the gelling agent and the encapsulant before mixing the solvent, fragrant agent, gelling agent and encapsulant.

3. The process of claim 1, further comprising the step of covering the cartridge housing opening with a seal.

4. The process of claim 3, further comprising the step of allowing the liquid blend to cool before covering the cartridge housing opening with the seal.

5. The process of claim 1, wherein the air permeable membrane has an air permeability of about 800 CFM/ft$^2$ to about 1200 CFM/ft$^2$ and a density between abut 0.3 oz/yd$^2$ and 0.9 oz/yd$^2$, the membrane being positioned above the gel so as to permit the fragrant agent to communicate with an environment external to the cartridge housing opening through the membrane at a release rate between about 0.70 to about 1.30 grams per day.

6. The process of claim 1, wherein the air permeable membrane has a density between about 0.5 oz/yd$^2$ to abut 0.7 oz/yd$^2$, and a permeability between about 900 CFM/ft$^2$ to about 1100 CFM/ft$^2$, wherein the fragrance communicates with the environment at a release rate between about 0.9 grams per day to about 1.10 grams per day over a period of about twenty-five days.

* * * * *